(12) United States Patent
Goodman

(10) Patent No.: US 8,965,020 B2
(45) Date of Patent: Feb. 24, 2015

(54) SOUND PROCESSORS WITH LIGHT TRANSMISSIVE SEALS AND IMPLANTABLE COCHLEAR STIMULATION SYSTEMS INCLUDING THE SAME

(75) Inventor: James P. Goodman, Valencia, CA (US)

(73) Assignee: Advanced Bionics AG, Staefa (CH)

( * ) Notice: Subject to any disclaimer, the term of this patent is extended or adjusted under 35 U.S.C. 154(b) by 103 days.

(21) Appl. No.: 13/990,036

(22) PCT Filed: Dec. 16, 2011

(86) PCT No.: PCT/US2011/065608
§ 371 (c)(1),
(2), (4) Date: Jul. 23, 2013

(87) PCT Pub. No.: WO2012/083229
PCT Pub. Date: Jun. 21, 2012

(65) Prior Publication Data
US 2013/0301859 A1    Nov. 14, 2013

Related U.S. Application Data

(60) Provisional application No. 61/424,582, filed on Dec. 17, 2010.

(51) Int. Cl.
*H04R 25/00*    (2006.01)
*G06F 3/00*    (2006.01)
*A61N 1/08*    (2006.01)
(Continued)

(52) U.S. Cl.
CPC    *H04R 25/65* (2013.01); *A61N 1/08* (2013.01); *A61N 1/375* (2013.01); *H04R 25/60* (2013.01); *G06F 1/1656* (2013.01); *A61N 1/36032* (2013.01)
USPC ............ 381/322; 381/324; 381/330; 715/865

(58) Field of Classification Search
CPC ...... H04R 25/30; H04R 25/60; H04R 25/608; H04R 25/65; H04R 2225/63; F21V 23/008; G06F 1/1656
USPC ......... 381/327, 324, 330; 600/25; 607/56–57; 715/865
See application file for complete search history.

(56) References Cited

U.S. PATENT DOCUMENTS 3,732,389 A   5/1973   Kaelin et al.
4,191,873 A   3/1980   Woodard
(Continued)

FOREIGN PATENT DOCUMENTS

EP    2012573 A2    1/2009
EP    2012573 A3    2/2009

OTHER PUBLICATIONS

PCT Search Report and Written Opinion dated Mar. 23, 2012 for PCT App. Ser. No. PCT/US2011/065608.

*Primary Examiner* — Jesse Elbin
(74) *Attorney, Agent, or Firm* — Henricks, Slavin & Holmes LLP

(57) ABSTRACT

Sound processors with light transmissive seals and systems including such sound processors are disclosed. A seal, formed in part from substantially translucent material and having at least a portion of the substantially translucent material associated with the housing exterior of the sound processor, transmits light from a light emitter carried within the housing to indicate an operational aspect of the sound processor.

19 Claims, 9 Drawing Sheets

(51) Int. Cl.
*A61N 1/375* (2006.01)
*G06F 1/16* (2006.01)
*A61N 1/36* (2006.01)

(56) References Cited

U.S. PATENT DOCUMENTS

| | | |
|---|---|---|
| 5,053,591 A | 10/1991 | Theurer |
| 5,824,022 A | 10/1998 | Zilberman et al. |
| 6,874,921 B2 | 4/2005 | Verlagte et al. |
| 7,503,790 B2 | 3/2009 | Bodmann et al. |
| 2003/0007656 A1* | 1/2003 | Verweg .................. 381/172 |
| 2004/0044383 A1 | 3/2004 | Woods et al. |
| 2006/0062012 A1 | 3/2006 | Tsai |
| 2007/0106344 A1 | 5/2007 | Darley et al. |
| 2007/0259594 A1* | 11/2007 | Galbiati et al. .................. 446/15 |
| 2009/0008880 A1 | 1/2009 | Bodmann et al. |
| 2010/0046779 A1 | 2/2010 | Crawford |

\* cited by examiner

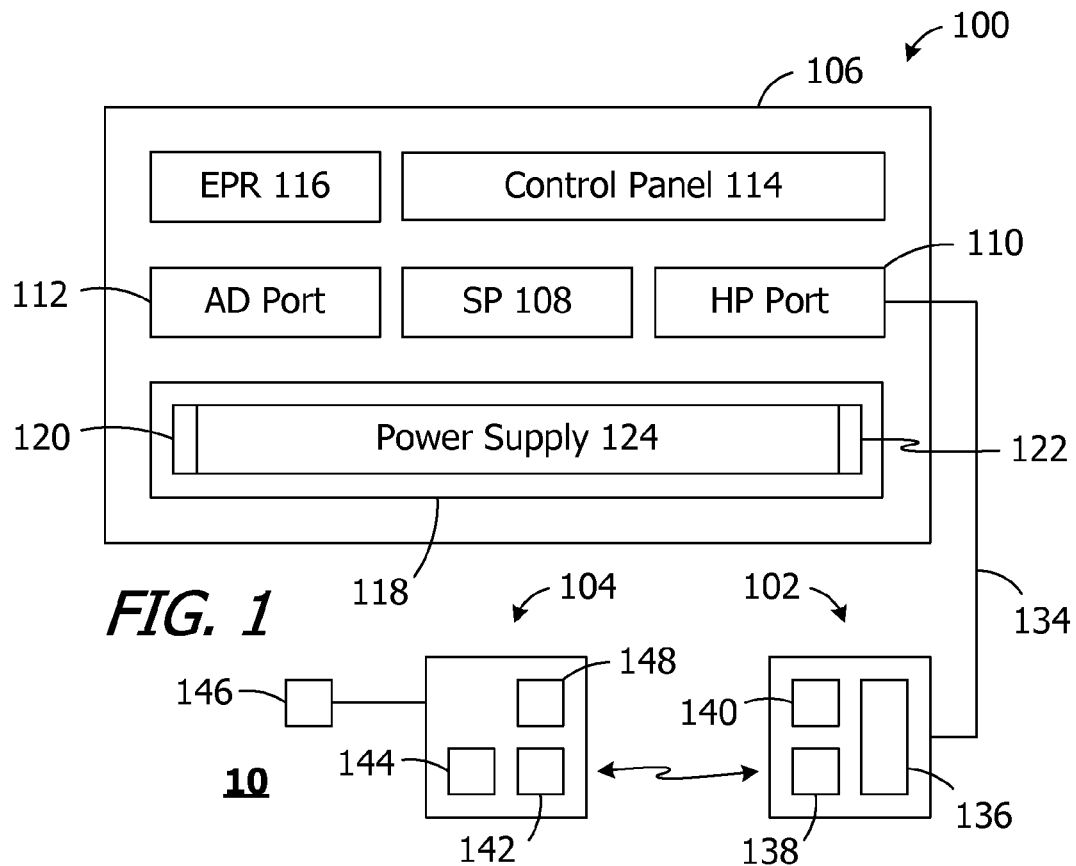
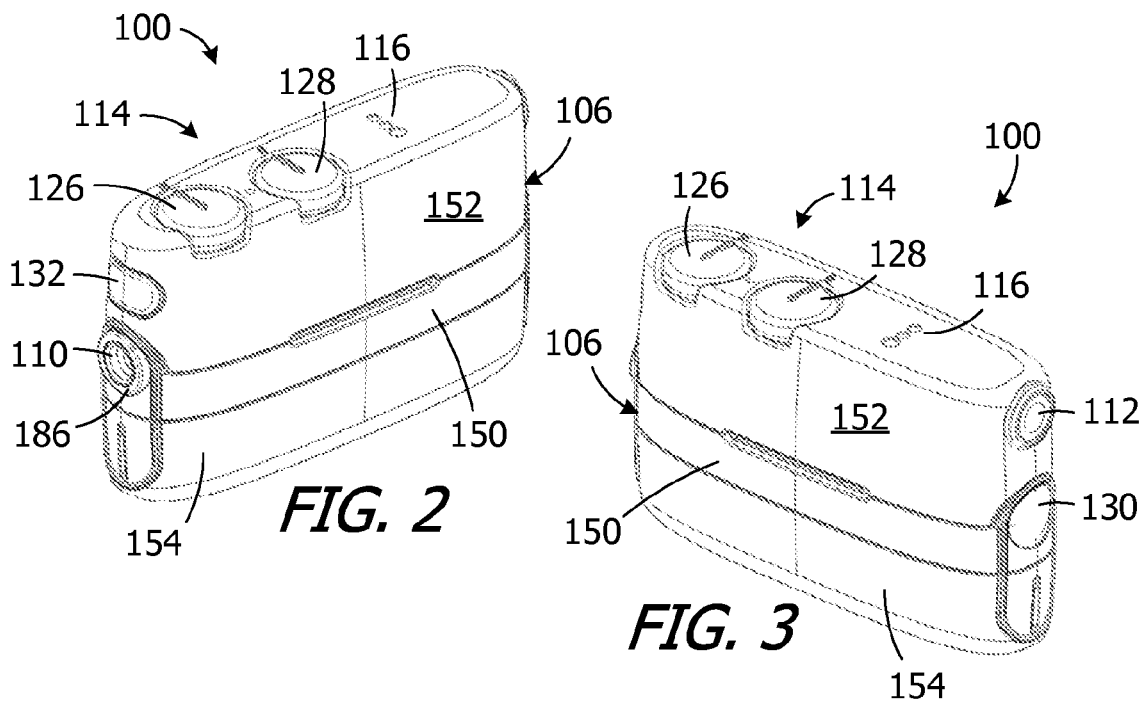

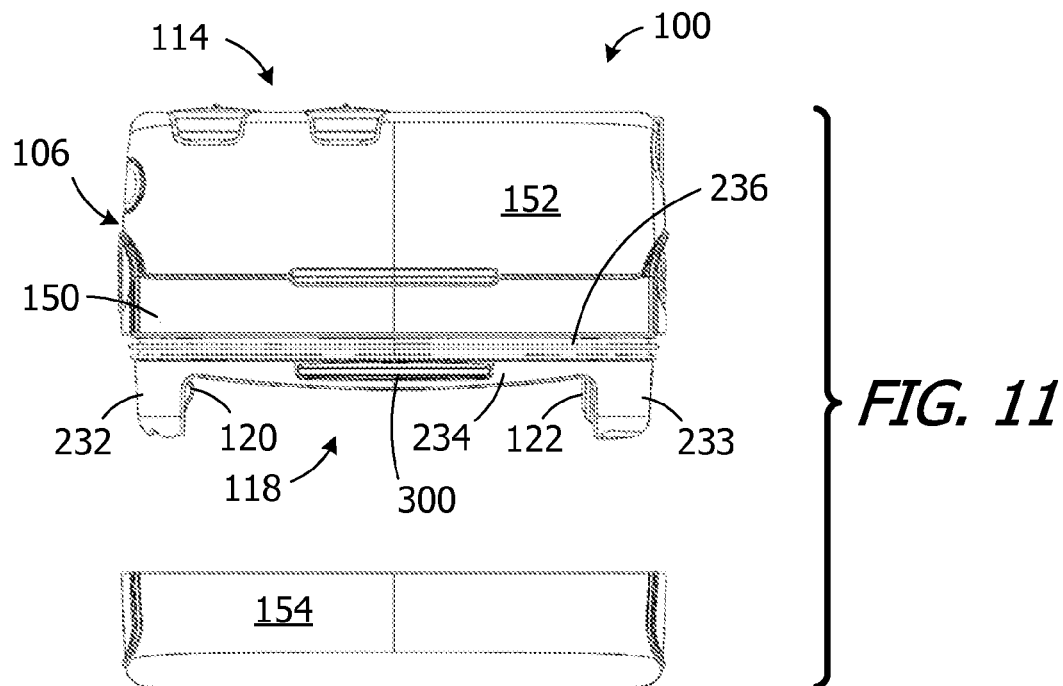
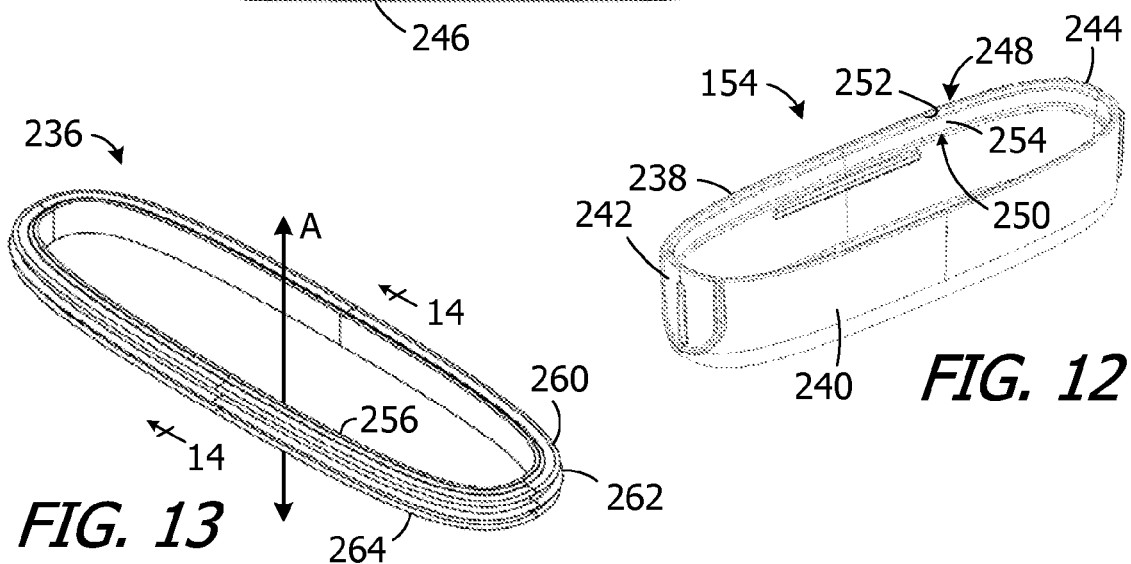
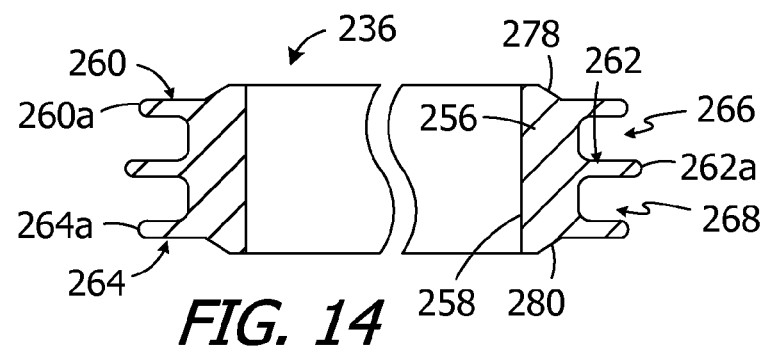

SOUND PROCESSORS WITH LIGHT TRANSMISSIVE SEALS AND IMPLANTABLE COCHLEAR STIMULATION SYSTEMS INCLUDING THE SAME

CROSS-REFERENCE TO RELATED APPLICATIONS

This application is the U.S. National Stage of PCT App. Ser. No. PCT/US2011/065608, filed Dec. 16, 2011, which claims priority to U.S. Prov. App. Ser. No. 61/424,582, filed Dec. 17, 2010.

BACKGROUND

1. Field

The present disclosure relates generally to sound processors such as, for example, the sound processors in implantable cochlear stimulation (or "ICS") systems.

2. Description of the Related Art

ICS systems are used to help the profoundly deaf perceive a sensation of sound by directly exciting the intact auditory nerve with controlled impulses of electrical current. Ambient sound pressure waves are picked up by an externally worn microphone and converted to electrical signals. The electrical signals, in turn, are processed by a sound processor, converted to a pulse sequence having varying pulse widths and/or amplitudes, and transmitted to an implanted receiver circuit of the ICS system. The implanted receiver circuit is connected to an implantable electrode array that has been inserted into the cochlea of the inner ear, and electrical stimulation current is applied to varying electrode combinations to create a perception of sound. A representative ICS system is disclosed in U.S. Pat. No. 5,824,022, which is entitled "Cochlear Stimulation System Employing Behind-The-Ear Sound processor With Remote Control" and incorporated herein by reference in its entirety.

As alluded to above, some ICS systems include an implantable device, a sound processor unit, and a microphone that is in communication with the sound processor unit. The implantable device communicates with the sound processor unit and, to that end, some ICS systems include a headpiece that is in communication with both the sound processor unit and the implantable device. In one type of ICS system, the sound processor unit is worn behind the ear (a "BTE unit"), while other types of ICS systems have a body worn sound processor unit (or "body worn unit"). The body worn unit, which is larger and heavier than a BTE unit, is typically worn on the user's belt or carried in the user's pocket. In those instances where body worn units have a replaceable battery, the body worn unit housing will have a battery compartment (or "receptacle") and a removable battery compartment cover. One example of a conventional body worn unit is the Advanced Bionics Platinum Series body worn unit.

Sound processor housings frequently include a visible status indicator, such as an LED, that is used to provide information about the operation of the sound processor (e.g. on/off status, battery status, and headpiece lock status). Such a status indicator requires an opening in the sound processor housing for a light emitter, as well as a seal to prevent dust and moisture from entering the housing by way of any space between the light emitter and housing. The present inventor has determined that visible status indicators may be more efficiently and effectively provided.

SUMMARY

A sound processor in accordance with one embodiment of a present invention includes a housing, a seal formed from at least substantially translucent material and having at least a portion thereof associated with the housing exterior, and a light emitter carried within housing that directs light into the seal. The present inventions also include cochlear stimulation systems with a cochlear implant and such a sound processor.

A sound processor in accordance with one embodiment of a present invention includes a housing, a device carried by the housing such that a gap is defined between a portion of the housing and a portion of the device, a light emitter within the housing, and means for sealing the gap against the ingress of moisture while permitting transmission of light through the gap. The present inventions also include cochlear stimulation systems with a cochlear implant and such a sound processor.

A method in accordance with one embodiment of a present invention includes the step of transmitting visible light that is representative of an operational aspect of the sound processor through a seal associated with the sound processor housing.

Such sound processors, systems and methods are advantageous for a variety of reasons. For example, construction of the sound processor is simplified. One otherwise necessary structure (e.g., a seal for a device associated with the housing exterior) is used to eliminate the need for other structures (e.g., the housing opening and seal associated with conventional status indicators).

The above described and many other features of the present inventions will become apparent as the inventions become better understood by reference to the following detailed description when considered in conjunction with the accompanying drawings.

BRIEF DESCRIPTION OF THE DRAWINGS

Detailed descriptions of the exemplary embodiments will be made with reference to the accompanying drawings.

FIG. 1 is a functional block diagram of an ICS system in accordance with one embodiment of a present invention.

FIG. 2 is a perspective view of a sound processor in accordance with one embodiment of a present invention.

FIG. 3 is a perspective view of a sound processor in accordance with one embodiment of a present invention.

FIG. 11 is an exploded side view of a sound processor in accordance with one embodiment of a present invention.

FIG. 12 is a perspective view of a power supply receptacle cover in accordance with one embodiment of a present invention.

FIG. 13 is a perspective view of a seal in accordance with one embodiment of a present invention.

FIG. 14 is a section view taken along line 14-14 in FIG. 13.

DETAILED DESCRIPTION OF THE EXEMPLARY EMBODIMENTS

Figure 4:
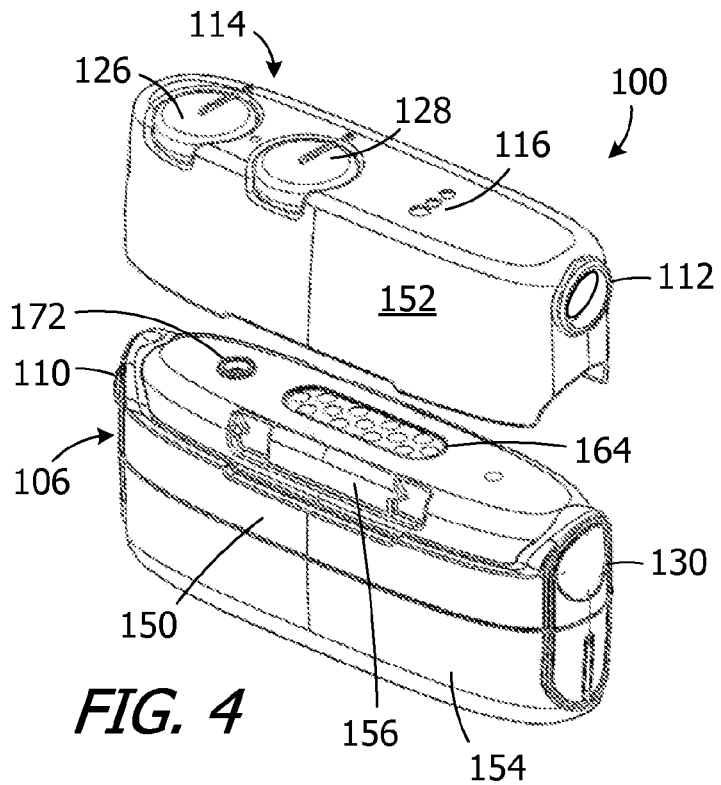
FIG. 4 is an exploded perspective view of a sound processor in accordance with one embodiment of a present invention.

The following is a detailed description of the best presently known modes of carrying out the inventions. This description is not to be taken in a limiting sense, but is made merely for the purpose of illustrating the general principles of the inventions.

The present inventions have application in a wide variety of systems that provide sound (i.e. either sound or a perception of sound) to the hearing impaired as well as others who require such systems on a situational basis. One example of such a system is an ICS system where an external sound processor communicates with a cochlear implant and, accordingly, the present inventions are discussed in the context of ICS systems. The present inventions are not, however, limited to ICS systems and may be used in combination with other systems for the hearing impaired that currently exist, or are yet to be developed.

One example of a sound processor is the body worn sound processor ("sound processor") generally represented by reference numeral 100 in FIGS. 1-3. The exemplary sound processor 100, which may be combined with a headpiece 102 and a cochlear implant 104 to form an ICS system 10, includes a housing 106 in which and/or on which various components are supported. Such components may include, but are not limited to, sound processor circuitry 108, a headpiece port 110, an auxiliary device port 112 for an auxiliary device such as a mobile phone or a music player, a control panel 114, a Euro Plug receptacle 116 (for a Euro Plug such as that associated with the Phonak MLxi FM receiver), and a power supply receptacle 118 with electrical contacts 120 and 122 for a removable battery or other removable power supply 124 (e.g. rechargeable and disposable batteries or other electrochemical cells). Power supply receptacles are also sometimes referred to as "battery compartments" when they are intended for use with a battery. The headpiece port 110 and auxiliary device port 112 may be connected to the sound processor circuitry 108 by way of, for example, a signal splitter/combiner (not shown) such as that found in the Platinum Signal Processor body worn unit from Advanced Bionics Corporation. In the illustrated embodiment, the control panel 114 includes a volume knob 126 and a program switch 128. A power button 130 and a bayonet release button 132 are also carried on the housing 106. The bayonet release button 132 actuates a bayonet mechanism to release the housing control portion 152 from the housing main portion 150 (described below).

The headpiece 102 in the exemplary ICS system 10 includes a cable 134 which may be connected to the headpiece port 110, a microphone 136, an antenna 138 and a positioning magnet 140. The exemplary cochlear implant 104 includes an antenna 142, an internal processor 144, a cochlear lead 146 with an electrode array, and a positioning magnet (or magnetic material) 148. The transmitter 138 and receiver 142 communicate by way of electromagnetic induction, radio frequencies, or any other wireless communication technology. The positioning magnet 140 and positioning magnet (or magnetic material) 148 maintain the position of the headpiece antenna 138 over the cochlear implant antenna 142. During use, the microphone 136 picks up sound from the environment and converts it into electrical impulses, and the sound processor 100 filters and manipulates the electrical impulses and sends the processed electrical signals through the cable 134 to the transmitter 138. Electrical impulses received from an auxiliary device are processed in essentially the same way. The receiver 142 receives signals from the transmitter 138 and sends the signals to the cochlear implant internal processor 144, which modifies the signals and passes them through the cochlear lead 146 to the electrode array. The electrode array may be wound through the cochlea and provides direct electrical stimulation to the auditory nerves inside the cochlea. This provides the user with sensory input that is a representation of external sound waves which were sensed by the microphone 136.

It should be noted that, in other implementations, communication between the sound processor and a headpiece and/or auxiliary device may be accomplished through wireless communication techniques. It should also be noted that, in other implementations, the sound processor may be configured to directly communicate with the cochlear implant (i.e. without a headpiece and associated cable).

The exemplary sound processor 100 may be carried by the user in a variety of ways. By way of example, but not limitation, the sound processor 100 may be carried in the user's pocket, secured to a belt with a belt clip that is either part of housing 106 or a separate carrier, or placed in a harness that is configured to be worn by a small child.

Referring more specifically to FIGS. 2 and 3, the exemplary housing 106 includes a main portion 150, a control portion 152 and a power supply receptacle cover ("PSR cover") 154 that may be latched or otherwise detachably connected to the housing main portion 150 in the manner described below. The housing main portion 150 supports and/or houses the sound processor circuitry 108, headpiece port 110 and power button 130, and includes the power supply receptacle 118. The control portion 152 supports and/or houses the auxiliary device port 112, control panel 114, Euro Plug receptacle 116 and bayonet release button 132. In other words, in the exemplary implementation, the main portion 150 supports and/or houses those elements of the sound processor 100 that are required for the ICS system 10 to function, while the control portion 152 includes various elements that are only required from time to time (e.g. the volume knob 126) or are merely useful options (e.g. the auxiliary device port 112).

Figures 5, 6:
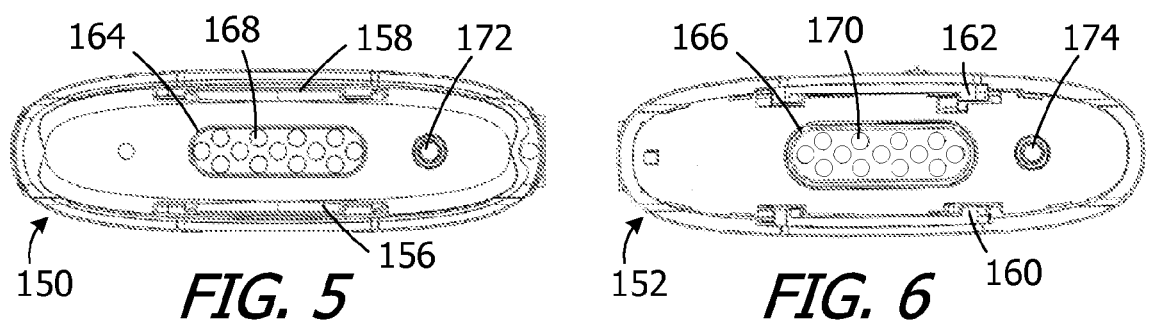
FIG. 5 is a plan view of a portion of a sound processor in accordance with one embodiment of a present invention.
FIG. 6 is a plan view of a portion of a sound processor in accordance with one embodiment of a present invention.
Figure 7:
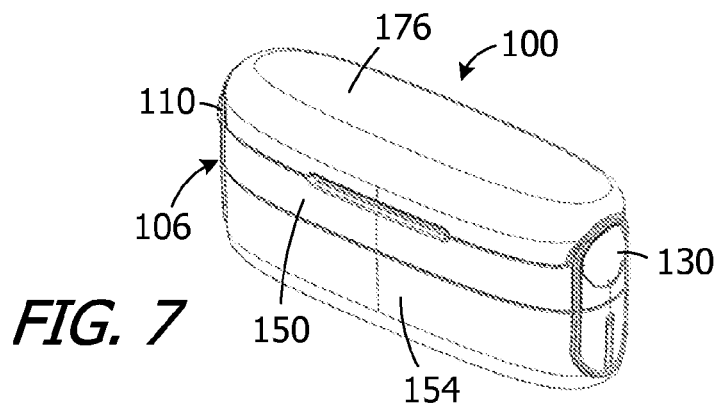
FIG. 7 is a perspective view of a sound processor in accordance with one embodiment of a present invention.

In the exemplary implementation, the sound processor 100 is configured such that the housing control portion 152 (and the functional elements associated therewith) may be mechanically and electrically separated from the housing main portion 150 (and the functional elements associated therewith) in the manner illustrated in FIG. 4. To that end, and referring also to FIGS. 5 and 6, the housing main portion 150 includes mechanical connectors 156 and 158 that are configured to mate with corresponding connectors 162 and 160, respectively, on the housing control portion 152. The housing main portion 150 and control portion 152 also include electrical connectors 164 and 166 with a plurality of contacts 168 and 170. An alignment locater feature, such as a post 172 and an opening 174 that receives the post and keys orientation, is also provided. Turning to FIG. 7, the sound processor 100 also includes a cover 176, with the same mechanical connectors (not shown) as the control portion 152, that may be used to protect the electrical connector 164 when the control portion is not in use.

It should also be noted here that, in other implementations, the sound processor may be configured such that the housing main portion and housing control portion define a single, integral unit that may not be separated in the manner described above.

The main portion 150 and control portion 152 of the exemplary housing 106 may be formed from relatively hard, rigid materials. A relatively hard material (as compared to the seals 186 and 212 discussed below) is a material that has a hardness greater than 75 Shore D. Suitable materials include, but are not limited to, a polycarbonate (PC), an acrylonitrile butadiene styrene (ABS), nylon and PC/ABS blends and various combinations thereof. One specific example is Lexan® Resin HP1R, from SABIC Innovative Plastics Company, which is a polycarbonate that has a hardness of about 70 Rockwell M. Another specific example is Noryl® PPO, a modified polyphenylene oxide. In one exemplary implementation, the main portion 150 may include a main structure formed from Lexan® Resin HP1R and a decorative overmold formed from a platable grade of PC/ABS with a chrome plating on the PC/ABS.

Figure 8:
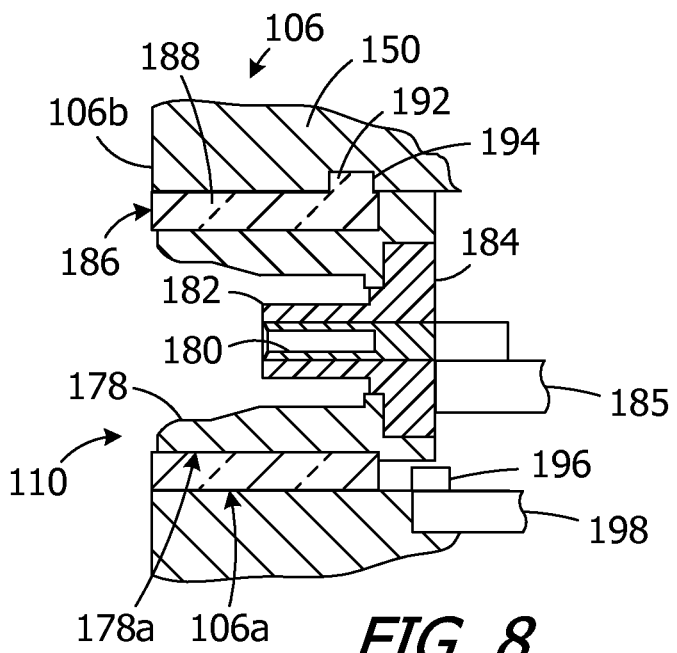
FIG. 8 is a section view of a port and seal in accordance with one embodiment of a present invention.
Figure 8A:
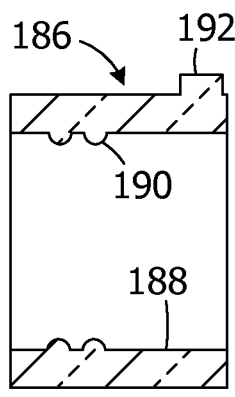
FIG. 8A is a section view of the seal illustrated in FIG. 8 in an uncompressed state.

Turning to FIGS. 8 and 8A, the exemplary headpiece port 110 includes a barrel 178 with a cylindrical exterior surface 178a, a socket 180, and insulators 182 and 184. In the illustrated embodiment, the headpiece port 110 is carried on a circuit board 185. The barrel 178 and socket 180 may be formed from suitable electrically conductive materials such as, for example, beryllium copper or brass. Thus, the barrel 178 is relatively rigid. The insulators 182 and 184 may be formed from a dielectric material such as, for example, polytetrafluoroethylene (PTFE). One example of such a headpiece port is available from IntelliConnect USA, LLC (part no. 5171-J1EG-000-100).

A resilient, elastomeric seal 186 is compressed in the gap between the housing 106 (here, the housing main portion 150) and the headpiece port 110 and, more specifically, between the housing and the barrel 178. Although the seal 186 is not limited to any particular configuration, the exemplary embodiment includes a hollow cylindrical portion (i.e. a portion with an annular cross-section) 188 that is compressed between the cylindrical outer surface 178a of the barrel 178 and a cylindrical inner surface 106a of the associated portion of the housing. The overall shape of the seal 186 will typically be dictated by the region to be sealed and may be, for example, other hollow geometric shapes in cross-section, solid geometric shapes in cross-section, or simply flat, depending on the shape of the gap being sealed.

The exemplary seal 186 illustrated in FIGS. 8 and 8A also has one or more inwardly projecting protrusions 190. Alternatively, or in addition, there may be one or more protrusions (not shown) that project radially outwardly from the cylindrical portion 188. The protrusions 190 are compressed during assembly, thereby insuring an effective seal between the seal 186 and both the housing 106 and the headpiece port barrel 178. A positioning tab 192 may be located near one end of the cylindrical portion 188 and a corresponding indentation 194 may be provided on the housing 106.

In the context of the present application, a "seal" is an elastomeric structure that is formed from material which is softer than, and may be compressed between, the structures between which the seal is being formed. The exemplary seal 186 is formed from a material that is softer than the associated portion of the housing 106 (here, the housing main portion 150) and the headpiece port barrel 178. As a result, the seal 186 may be compressed between the structures to form a barrier that will prevent dust and moisture from entering the sound processor 100 by way of the space between the housing 106 and the headpiece port barrel 178 that is occupied by the seal. Such a seal should have a sealing effectiveness of at least IEC IPX7. Suitable materials for the seal 186 and the seal 212 (discussed below) include, but are not limited to, silicone, urethane, and soft polyvinyl chloride (PVC) with a hardness of about 40-80 Shore A. In some implementations, the hardness of the seal material may be about 68±5 Shore A.

The exemplary seal 186 is also at least substantially translucent, and may be at least substantially transparent, and may be transparent. A light emitter 196 (FIG. 8) is positioned within the housing 106 and adjacent to the seal 186 on a circuit board 198. The configuration of the light emitter 196, as well as the location and orientation of the light emitter relative to the seal 186, are such that light emitted by the light emitter will be transmitted through the seal to the housing exterior 106b. The light will, therefore, be visible from outside the sound processor housing 106. A wide variety of light emitters may be employed. In the illustrated embodiment, the light emitter 196 is a right angle, multi-color LED that is able transmit green, red and orange light. Other suitable light emitters include, but are not limited to incandescent lamps and electroluminescent lamps.

The ability of the seal 186 to transmit light from the light emitter 196 allows the seal to be used, in conjunction with the light emitter, to provide visible information to a user that is representative of operational parameters of the sound processor 100. The light emitter 196 may be controlled by the sound processor circuitry 108 or other suitable control circuitry. By way of example, but not limitation, the exemplary sound processor 100 employs light (including a lack of light) to provide information to the user in the following manner. No light is emitted through the seal 186 when the sound processor is turned off or when the sound processor is operating properly, and there is no information to make the user aware of, after the initial startup. Solid (i.e. non-blinking) green light is emitted by the light emitter 196 and through the seal 186 when the sound processor is in test mode during start up. Orange blinking light emitted by the light emitter 196 and through the seal 186 is indicative of battery status, with the number of blinks (e.g. 1 to 4 blinks within a predetermined period) being indicative of the battery level. Solid orange light emitted by the light emitter 196 and through the seal 186 indicates that the battery is very low. Blinking green light is emitted by the light emitter 196 and through the seal 186 is used to show that audio signals are being processed normally. Blinking red light is emitted by the light emitter 196 and through the seal 186 when there is a loss of lock, i.e. when the headpiece is magnetically detached from the implanted cochlear stimulator. Solid red light is emitted by the light emitter 196 and through the seal 186 when there is a failure mode that requires restarting of the sound processor 100.

As illustrated above, the seal 186 simultaneously performs a sealing function (i.e. preventing ingress of dust and moisture) and a light transmission function. One exemplary advantage such a seal is that it simplifies construction of the sound processor 100. In particular, one otherwise necessary structure (i.e. a seal for headpiece port 110) is used to eliminate the need for other structures. Here, an opening in the housing for a light emitter, as well as the associated seal, may be omitted because the at least substantially translucent seal 186 for the headpiece port 110 allows light that is generated within the housing 106 to be viewed from outside the housing.

Figure 8B:
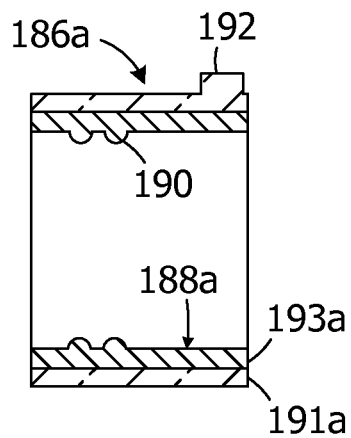
FIG. 8B is a section view of a seal in accordance with one embodiment of a present invention.
Figure 8C:
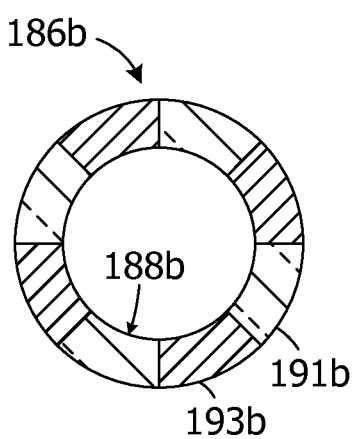
FIG. 8C is a section view of a seal in accordance with one embodiment of a present invention.

Other exemplary seals may be configured such that there is at least one portion that is at least substantially translucent and at least one portion that is opaque. By way of example, but not limitation, the exemplary seal 186a illustrated in FIG. 8B includes a cylindrical portion 188a with an at least substantially translucent cylindrical section 191a and an opaque cylindrical section 193a. The exemplary seal 186b illustrated in FIG. 8C includes a cylindrical portion 188b with a plurality of at least substantially translucent arcuate sections 191b and a plurality of opaque arcuate sections 193b that together form a cylinder.

Figure 9:
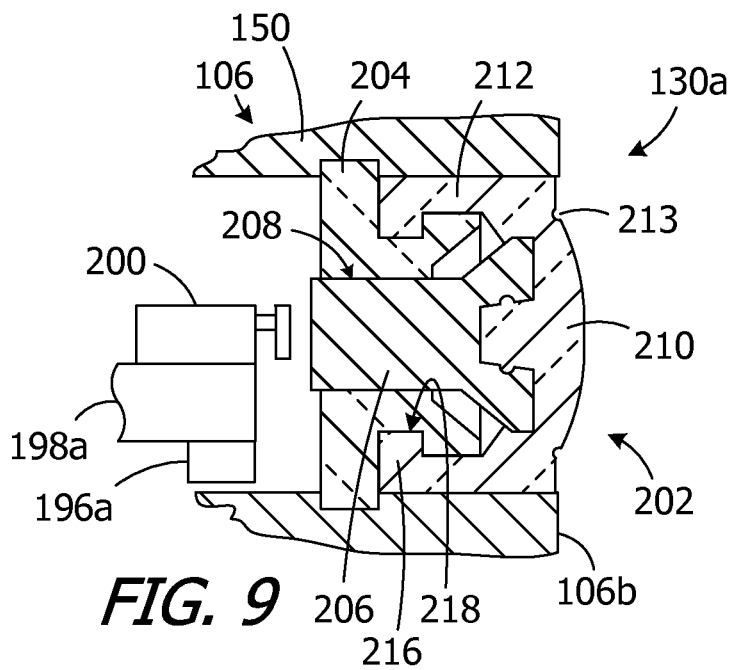
FIG. 9 is a section view of a button/seal in accordance with one embodiment of a present invention.
Figure 9A:
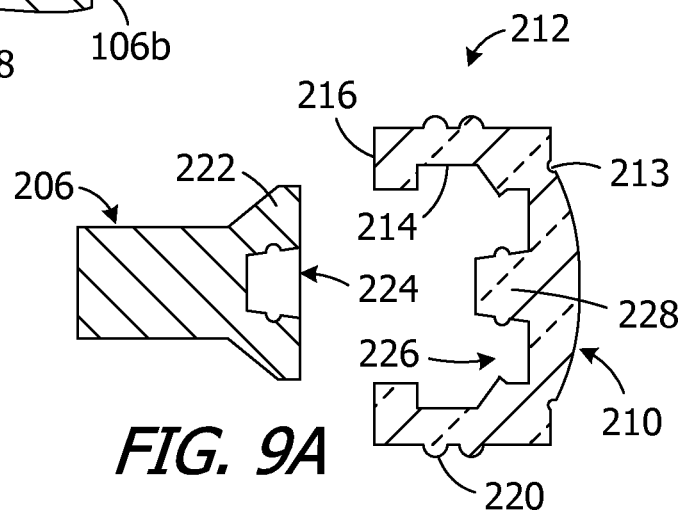
FIG. 9A is a section view of portions of the button/seal illustrated in FIG. 9.

Another example of a seal through which light may be transmitted is associated with the button 130a illustrated in FIGS. 9 and 9A, which may be employed in place of the button 130 illustrated in FIGS. 2 and 3. The exemplary button 130a includes a switch 200 and an actuator 202. The actuator 202 may have a base 204 that is secured to the housing 106, a piston 206 that slides within an aperture 208 that extends through the base, an external portion 210 that carries the piston, and a seal 212 that is mounted on the base. The external portion 210 and seal 212, which may be integrally formed (as shown) or separate structures that are joined to one another, are resilient and elastomeric and are separated by an indentation 213. The external portion 210 is also biased to the rest position illustrated in FIG. 9 that holds the piston 206 out of contact with the switch 200. The exemplary button 130a is actuated when a user presses the external portion 210, which the flexes until piston 206 engages (and closes) the switch 200. The external portion 210 will return to the rest position when the user releases the button 130a.

The exemplary seal 212 is compressed in the gap between the housing 106 (here, the housing main portion 150) and the button base 204. Although the seal 212 is not limited to any particular configuration, the exemplary embodiment includes a cylindrical portion 214, an annular portion 216 that is mounted within an annular recess 218 in the base 204, and one or more outwardly projecting protrusions 220. Alternatively, or in addition, there may be one or more protrusions (not shown) that project inwardly from the cylindrical portion 214. The protrusions 220 are compressed during assembly, thereby insuring an effective seal between the seal 212 and both the housing 106 and the button base 204.

The piston 206 may be secured to the button external portion 210 in a variety of ways. In the illustrated embodiment, the piston includes a head 222 and a connector 224 and the external portion includes a corresponding recess 226 and connector 228.

Figure 10:
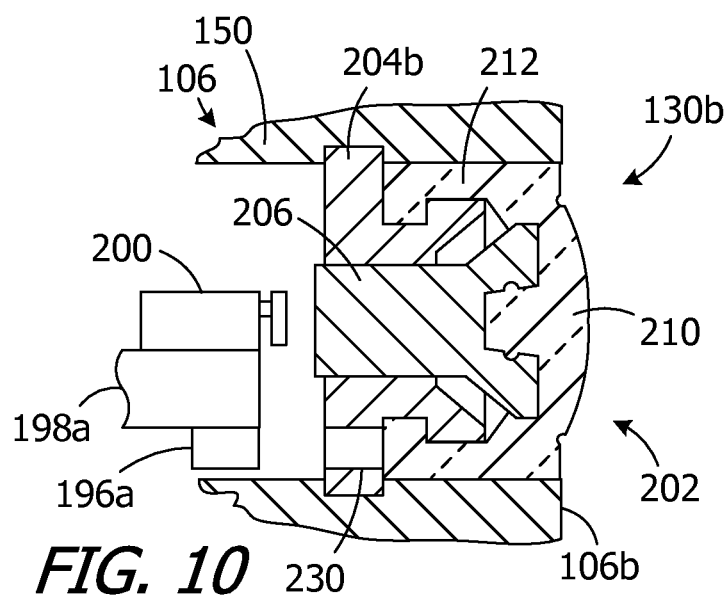
FIG. 10 is a section view of a button/seal in accordance with one embodiment of a present invention.

The exemplary seal 212 is at least substantially translucent, and may be at least substantially transparent, and may be transparent. A light emitter 196a is positioned within the housing 106 and adjacent to the seal 212 on a circuit board 198a. The configuration of the light emitter 196a, as well as the location and orientation of the light emitter relative to the seal 212, are such that light emitted by the light emitter will be transmitted through the seal to the housing exterior 106b and will, therefore, be visible from outside the sound process housing 106. The exemplary light emitter 196a may a right angle, multi-color LED that is able transmit green, red and orange light or some other light emitting device. It should be noted here that the base 204 in the exemplary embodiment illustrated in FIGS. 9 and 9A is at least substantially translucent, may be at least substantially transparent, and may be transparent. Thus, light from the light emitter 196a passes through both the base 204 and the seal 212. Alternatively, as illustrated in FIG. 10, an otherwise identical button 130b may be provided with an at least substantially opaque (or opaque) base 204b that includes an aperture 230 that is positioned between the light emitter 196a and the seal 212. In either case, the light will be visible at the housing exterior 106b.

Here too, the seal 212 simultaneously performs a sealing function (i.e. preventing ingress of dust and moisture) and a light transmission function, and may be used to in conjunction with the light emitter to provide information about operational parameters of the sound processor 100 in the manner described above. One exemplary advantage such a seal is that it simplifies construction of the sound processor 100. In particular, one otherwise necessary structure (i.e. a seal for the button 130a) is used to eliminate the need for certain visible status indicator structures, as is described above.

The button external portion 210 in the exemplary implementation integral with, and formed from the same material as, the seal 212. As such, the light from the light emitter 196a also passes through the button external portion. In other implementations, the button external portion 210 may be formed from opaque material. The combination of the opaque button external portion 210 and the at least substantially translucent seal 212 will result in a ring of light around the external portion during light emission by the light emitter 196a.

Other button configurations may also be employed. For example, the piston 206 in buttons 130a and 130b may be at least substantially translucent, at least substantially transparent, or transparent. Here, the aperture 230 (FIG. 10) may be omitted. Also, the recess and protrusion respectively associated with the connectors 224 and 228 may be omitted.

Turning to FIG. 11, the power supply receptacle 118 in the exemplary embodiment is defined by various portions of the main portion housing 150. In particular, the main portion housing 150 has a pair of end walls 232 and 233 and a pair of side walls 234 and 235 (FIG. 21) that together define the volume, or at least a portion of the volume, in which a battery or other power supply is held. The electrical contacts 120 and 122 are carried on the end walls 232 and 233 and, in the exemplary embodiment, contact 120 is a resilient contact that is depressed as the battery or other power supply is positioned between the contacts. The resilient contact 120 presses against the battery or other power supply to hold it in place. The main portion housing 150 also has a connector apparatus 292, which is used to hold the PSR cover 154 in place as is discussed below with reference to FIGS. 19-26.

The exemplary sound processor 100 may be configured for use in or around water and, accordingly, may be configured so as to insure that the power supply receptacle 118 is waterproof. More specifically, a seal 236 may carried on the main portion housing 150 in the manner illustrated in FIG. 11. Although the present inventions are not limited to any particular seal, two exemplary seals are described below. Other seals that may be employed include, but are not limited to, seals with solid cross-sections such as solid o-ring seals.

The exemplary seal 236 is a resilient band that extends around the entire perimeter of the main portion housing 150 and contacts the entire perimeter of the inner surface of the PSR cover 154 with a relatively constant force that is sufficient to prevent ingress of liquid. Although the seal 236 is removable and replaceable, it is held in the illustrated location during use. It should also be noted that the seal 236 is compressed radially when the PSR cover 154 is moved from the detached/open state (FIG. 11) where the power supply receptacle is accessible to the attached/covered state (FIGS. 2-3) where the power supply receptacle is not accessible. Put another way, the seal 236 is compressed in a direction that is perpendicular or at least substantially perpendicular to the direction that the PSR cover 154 moves as it slides onto the main portion housing 150 and over the seal.

In at least some implementations, the configuration of the PSR cover 154 is such that it facilitates the controlled radial compression of the seal 236. To that end, and referring to FIGS. 11 and 12, the PSR cover 154 in the exemplary implementation includes side walls 238 and 240, end walls 242 and 244, a bottom wall 246 and an open end 248 opposite the bottom wall. The intersections of the side and end walls 238-244, and to some extent the side and end walls themselves, are curved. The cover walls in other implementations may define a rectangular shape with 90 degree corners. The exemplary PSR cover 154 also includes an inner surface 250, with a tapered transition portion 252 and a seal portion 254, that extends completely around the perimeter of the cover. The circumference of the inner surface 250 is greatest at the open end 248, then decreases through the transition portion 252 such that the slope is about 1.0 to about 1.7, and then is substantially constant in the seal portion 254. The transition portion 252 and seal portion 254 cooperate with the seal 236 in the manner described below with reference to FIG. 16.

As illustrated in FIGS. 13 and 14, the exemplary seal 236 includes a base member 256, which defines the inner surface 258 of the seal, and a plurality of protrusions 260-264 that extend outwardly from the base member and have longitudinal ends 260a-264a. The seal 236 is formed from resilient material and, as is illustrated in FIG. 13, defines a closed geometric overall shape (e.g. circular or the illustrated oval). The seal 236 is slightly smaller than the portion of the main portion housing 150 on which is it is to be supported. As a result, the seal 236 will be pre-stressed when placed on the housing to prevent ingress of liquid between the seal inner surface 258 and the housing. The exemplary seal 236 also includes material-free regions 266 and 268 that are respectively located between protrusions 260 and 262 and protrusions 262 and 264. The material free regions 266 and 268 provide open spaces (or "air gaps") into which portion of the seal deflects during the slide-on radial compression that occurs when the PSR cover 154 is secured to the main portion housing 150. Although the protrusions 260-264 are generally planar structures that extend radially outwardly and are perpendicular to the base member inner surface 258 in the illustrated embodiment, other configurations may be employed.

Figure 15:
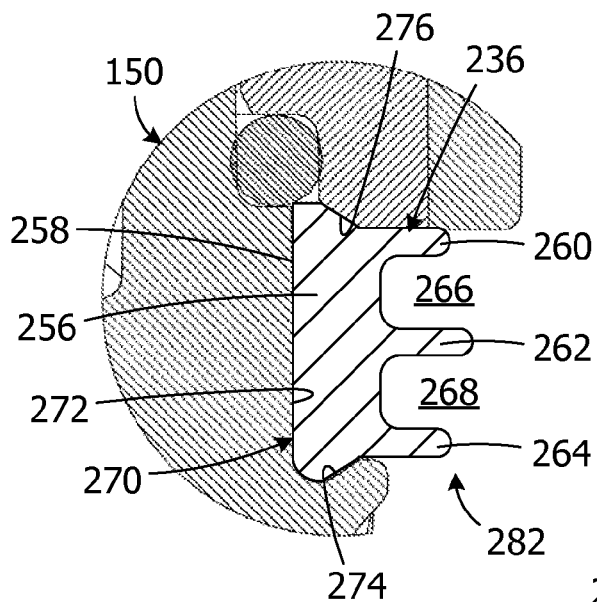
FIG. 15 is a section view of a portion of a sound processor main portion in accordance with one embodiment of a present invention with the power supply receptacle cover removed.
Figure 16:
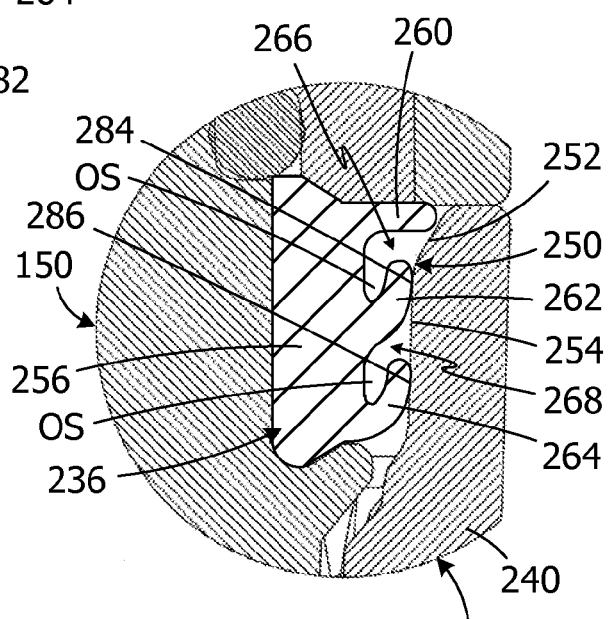
FIG. 16 is a section view of a portion of a sound processor main portion in accordance with one embodiment of a present invention with the power supply receptacle cover in place.

Turning to FIGS. 15 and 16, the exemplary main portion housing 150 has a channel 270 into which the seal 236 may be inserted. The channel 270 has an inner surface 272 that abuts the seal inner surface 240. The channel 270 also has a pair of inwardly projecting surfaces 274 and 276. The seal main portion 256 has corresponding surfaces 278 and 280 (FIG. 14). The seal 236 is stretched and deflected into the channel 270 during assembly and held in the channel 270 by the inwardly projecting surfaces 274 and 276. So arranged, the protrusions 260-264 will extend radially outwardly from the main portion 256 and one or more of the protrusions will be located within a region 282 that will ultimately be occupied by a portion of the PSR cover 154. As the PSR cover 154 in the exemplary implementation moves through the region 282, the inner surface transition portion 252 will sequentially engage and deflect the protrusions 264 and 262. When the PSR cover 154 reaches attached/covered state, which is illustrated in FIG. 16, the protrusions 262 and 264 will be deflected in the manner shown such that they engage the inner surface seal portion 254 at contact points 284 and 286 and there are open spaces OS between the protrusions and the main portion 256. Each contact point 284 and 286, which are the points at which radial force is applied to the seal 236, extends around the perimeter of the PSR cover 154 with enough force to prevent ingress of fluid.

Figure 17:
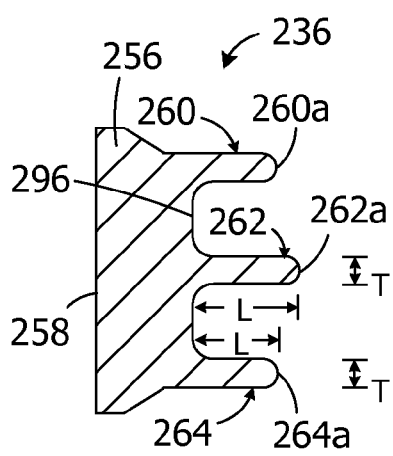
FIG. 17 is a section view of a seal in accordance with one embodiment of a present invention.

Although the protrusions 260-264 may be identical in some implementations, the protrusion 262 in the exemplary seal 236 is configured so as to have different structural characteristics than the protrusions 260 and 264. The differences in structural characteristics are differences that result in differences in sealing characteristics generally, and the creation of more sealing force at protrusion 262 in particular. Referring to FIG. 17, in the exemplary seal 236, the length L of the protrusion 262 is greater than the length of protrusion 264, while the thicknesses T of protrusions 262 and 264 are same. Given the fact that the distance between the seal base member 256 and the seal portion 254 of the PSR cover inner surface 250 is essentially the same at each protrusion, the protrusion 262 will undergo a greater degree of deflection and radial compression than the protrusion 264 because it is longer. As such, as despite the fact that the protrusions are the same thickness and formed from the same materials, the protrusion 262 will form a tighter seal than the protrusion 264 and will act as the primary portion of the seal. Locating the primary portion of the seal sufficiently away from the open end 248 is advantageous for insuring that the seal makes uniform radial contact with the PSR cover inner surface 250. The protrusion 264 functions as the secondary portion of the seal to prevent ingress of liquid should liquid pass the seal formed by protrusion 262. Such liquid will be at a lower pressure than liquid at the seal formed by protrusion 262.

It should be noted here that, given the respective dimensions of the protrusion 260 and the inner surface transition portion 252, the protrusion 260 does not create a seal or at least any substantial seal. The protrusion 260 may, therefore, be omitted in some embodiments. The protrusion 260, which is identical to protrusion 264, is included in the exemplary seal 236 for a number of other reasons. Most notably, the inclusion of the protrusion 260 makes the seal 236 symmetric about the protrusion 262 and, accordingly, it is reversible. If the seal 236 is mounted "upside down" on the housing 106, there will be no change in function and, in some instances, the life of the seal may be extended if it is removed and reversed after some period of use. The beam strength of the seal 236, as defined by the material thickness in the radial direction, is symmetric in the axial dimension. The additional beam strength associated with the protrusion 260 also improves the seal between the inner surface 258 and the inner surface 272 of the housing channel 270 created by the pre-stressing of the seal.

There are a variety of other ways to create protrusions with differing sealing characteristics. By way of example, but not limitation, differences in the respective thicknesses of the protrusions and/or materials used to form the protrusions may be employed alone or in combination with differences in other structural characteristics (e.g. length) to create protrusions having the desired differences in sealing characteristics.

Figure 18:
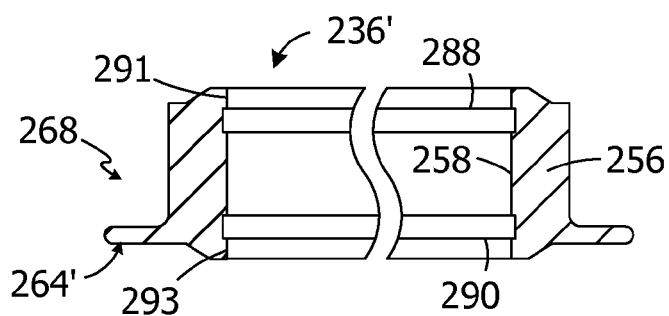
FIG. 18 is a section view of a seal in accordance with one embodiment of a present invention.
Figure 19:
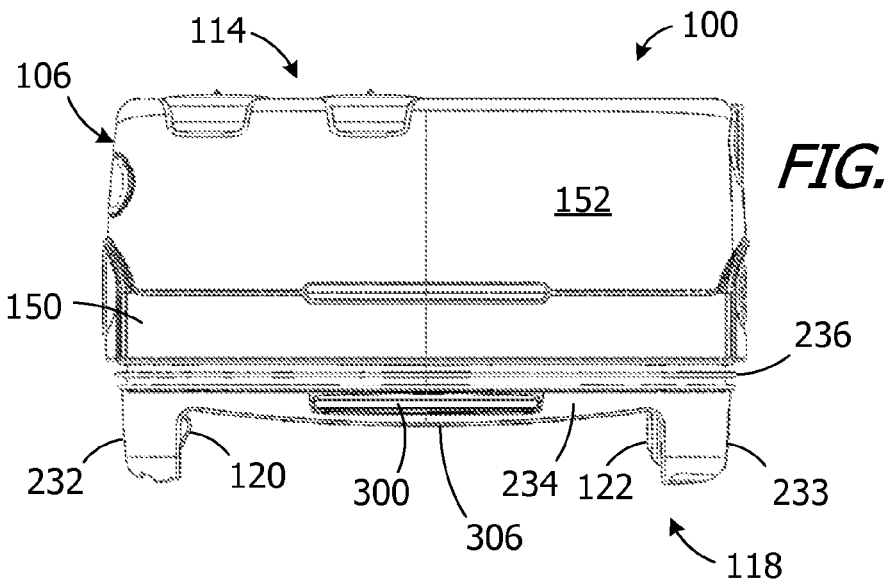
FIG. 19 is a side view of a sound processor in accordance with one embodiment of a present invention with the power supply receptacle cover removed.
Figure 20:
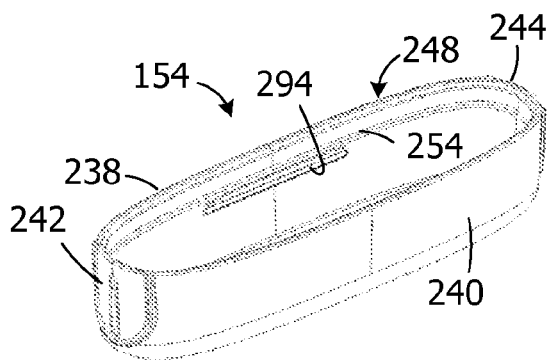
FIG. 20 is a perspective view of a power supply receptacle cover in accordance with one embodiment of a present invention.
Figure 29:
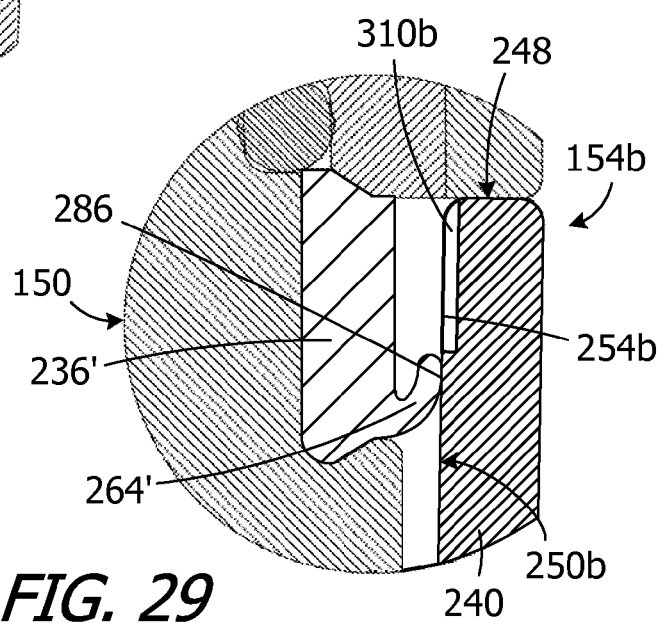
FIG. 29 is a section view of a portion of a sound processor main portion with the power supply receptacle cover in place.

Another exemplary seal, which is generally represented by reference numeral 236' in FIG. 18, and which is otherwise identical to seal 236, includes only a single protrusion 264', a single material free region 268, and one or more grooves, e.g. grooves 288 and 290, that are formed in the base member 256. The single protrusion 264' forms a seal in the manner described above in the context of protrusion 262 (FIGS. 15-16) and, in the illustrated embodiment, the single protrusion is the same length as the protrusion 262. In embodiments that include the seal 236', the inner surface of the associated PSR cover may include a tapered transition portion (e.g. transition portion 252 in FIG. 16), or as is illustrated in FIG. 29, the tapered transition portion may be omitted.

The grooves 288 and 290 are relatively shallow (e.g. about 0.004 inch), extend around the perimeter of the inner surface 258, and define relatively small (as compared to the entire surface 258) upper and lower contact surfaces 291 and 293 at the axial ends of the base member 256. The separate seals between the inner surface 258 and the inner surface 272 of the housing channel 270 formed at the spaced contact surfaces 291 and 293 are, in some instances, more readily controllable than a single seal formed from an inner surface without grooves. Although the profiles of the exemplary grooves 288 and 290 are rectangular in shape, grooves of other shapes may be employed. It should also be noted that grooves, such as grooves 288 and 290, may be added to the inner surfaces of each of the other seal embodiments described above and below if so desired.

With respect to materials, suitable resilient materials for the exemplary seals disclosed herein include but are not limited to silicone. The dimensions of the seals will depend on the desired characteristics and the dimensions of the main portion housing and PSR cover, and the present seals are not limited to any particular dimensions unless such dimension are set forth in the claims below. Referring to FIG. 13, the unstretched major and minor dimensions (measured perpendicular to the Axis A) of the exemplary seal 236 are about 53.00 mm to 57.00 mm and about 14.00 mm to 16.00 mm. Turning to FIG. 17, the thickness of the base member 256, i.e. the distance between inner surface 258 and outer surface 296, is about 0.90 mm to 1.00 mm, the height of the base member is about 2.80 mm to 3.80 mm, the protrusions 260-264 are about 0.30 mm to 0.50 mm thick, the protrusions 260 and 264 are about 0.80 mm to 1.00 mm long, and the length of protrusion 262 is about 1.00 mm to 1.20 mm.

The PSR cover and seal arrangements described above in the context of the illustrated embodiments are such that the waterproof rating at the PSR cover will be IPX7, i.e. there will be no ingress of visible water into the power supply receptacle 118 when the exemplary sound processor 100 is immersed in water at a depth of 1 meter for 30 minutes.

The exemplary sound processor 100 may also include a connector apparatus that secures the PSR cover 154 to the main portion housing 150. One example of such a connector apparatus is illustrated in FIGS. 19-22. Additionally, or alternatively, the sound processor 100 may be configured so as to insure that the PSR cover 154 must be gripped in a particular way to facilitate removal, as discussed in greater detail below with reference to FIGS. 23-26.

Figure 22:
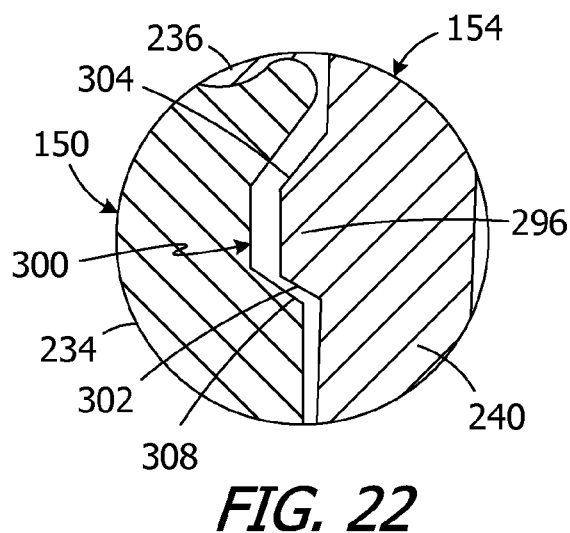
FIG. 22 is an enlarged view of a portion of FIG. 21.
Figure 21:
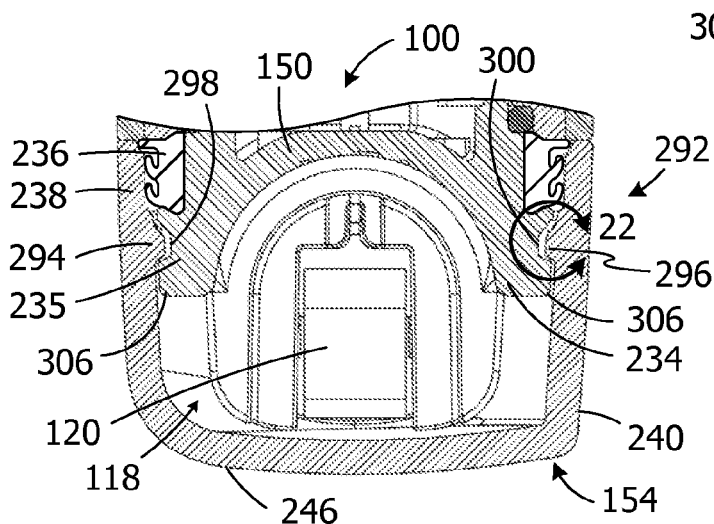
FIG. 21 is a section view of a portion of a sound processor in accordance with one embodiment of a present invention with the power supply receptacle cover in place.

As illustrated for example in FIGS. 19-22, the exemplary connector apparatus 292 (FIG. 21) includes protrusions 294 and 296, which are carried by the PSR cover walls 238 and 240, and are configured to mate with indentations 298 and 300 in the side walls 234 and 235 of main portion housing 150. Each of the protrusions 294 and 296 includes two cam surfaces 302 and 304 (FIG. 22), and each of the side walls 234 and 235 includes edges 306 (FIGS. 21-22). The resilience of the PSR cover 154 allows the side walls 238 and 240 to deflect as the cover moves from the detached/open state (FIGS. 19-20) to the attached/covered state (FIGS. 21-22) and from the attached/covered state to the detached/open state. More specifically, as the PSR cover 154 moves from the detached/open state toward the main portion housing 150, the cam surfaces 304 on the cover protrusions 294 and 296 will engage the edges 306 of housing walls 234 and 235. As the PSR cover 154 continues to move in this direction, the cover walls 238 and 240 will deflect radially outwardly, as permitted by the resilience of the PSR cover 154, while the protrusions 294 and 296 pass the edges 306. The PSR cover walls 238 and 240 will remain deflected radially outwardly until the protrusions 294 and 296 are aligned with the indentations 298 and 300. At this point, the resilience of the PSR cover 154 will cause the walls 238 and 240 to move radially inwardly such that the protrusions 294 and 296 are located within the indentations 298 and 300, in their radially retracted positions, thereby locking the cover in place. Conversely, when the PSR cover 154 pulled in the opposite direction, the cam surfaces 302 on the protrusions 294 and 296 will engage the edges 308 of the side walls 234 and 235. The cover walls 238 and 240 will deflect radially outwardly, to their radially extended positions, and the protrusions 294 and 296 will move out of the indentations 298 and 300 as the PSR cover 154 continues to be pulled away from the main portion housings 150.

The protrusions 294 and 296 and indentations 298 and 300 in the illustrated embodiment are also elongate and located at the longitudinally central region of the housing side walls 234 and 235 and PSR cover side walls 238 and 240. The longitudinally central region of the PSR cover side walls 238 and 240 is the region of maximum radial extension.

Suitable resilient materials for the PSR cover 154 include, but are not limited to PC/ABS resin. Such materials, in combination with a wall thickness of about 0.050 inch and the other dimension of the cover described herein will allow the PSR cover 154 to resiliently deflect in the manner described above. The main portion housing 150 and control portion housing 152 may be formed from the same materials, but will be stiffer due to the geometry.

It should be emphasized here that the connector apparatus 292 is merely one example of an apparatus that may be carried on the cover side walls 238 and/or 240 and used to secure the PSR cover 154 to the main portion housing 150. By way of example, but not limitation, an alternative PSR cover and main portion housing arrangement may be configured such that the locations of the above-described protrusions, indentations, cam surfaces and edges are reversed. Another alternative is to simply include a protrusion and indentation, along with the associated cam surfaces and edges, on one of the cover side walls 238 and 240. A connector apparatus similar to connector apparatus 292 may also be associated with the portion of the housing above (in the illustrated orientation) the seal and with the open end of the PSR cover, i.e. located on the other side of the seal. The protrusions and indentations may also have curved surfaces instead of the linear surfaces.

The overall configuration of the housing 106 may, in some implementations, be such that the PSR cover 154 is a child resistant cover. In particular, the dimensions of the housing 106 and the location of the connector apparatus (e.g. the protrusions 294 and 296 and the indentations 298 and 300) make it exceedingly difficult for a young child (e.g. infants and toddlers up to about 4 years of age) to remove the PSR cover 154.

Referring to FIGS. 23-26, and although the present inventions are not limited to such a configuration, the length L of the housing 106 in the illustrated embodiment is substantially greater than, e.g. at least about two times and in some instances at least about three times, the width W of the housing. The length L of the exemplary housing 106 is also relatively large. The "length" is the major dimension perpendicular to the axis A which, in the illustrated embodiment, is also perpendicular to direction of cover movement (note arrows B in FIG. 23). As used herein, "relatively large" means at least 2 inches, which is a length that a young child would find difficult to grip with sufficient force to remove the PSR cover 154. Exemplary values of the length L range from about 2 inches to about 4 inches, depending on the age of the child, and the illustrated embodiment is 2.3 inches long. The width W of the exemplary housing 106 is relatively small. The "width" is the minor dimension perpendicular to the axis A which, in the illustrated embodiment, is also to the direction of cover movement (note arrows E in FIG. 24). As used herein, "relatively small" means no more than 2 inches (e.g. when the length is 4 inches). Exemplary values of the width W range from about 0.25 inch to about 2 inches, and the illustrated embodiment is about 0.7 inches wide. The lengths of the main portion housing side walls 234 and 235 and the PSR cover side walls 238 and 240 closely correspond to, or are the same as, the length L of the housing 106, while the lengths of the main portion housing end walls 232 and 233 and the PSR cover end walls 242 and 244 closely correspond to, or are the same as, the width W of the housing 106. As noted above, the wall thickness of the PSR cover 154, in combination with the resiliency of the cover materials, facilitates the resilient radial deflection of the side walls 238 and 240.

Figure 23:
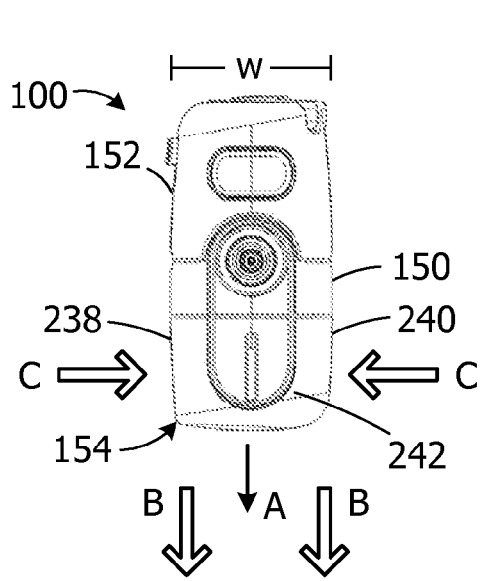
FIG. 23 is an end view of a sound processor in accordance with one embodiment of a present invention.
Figure 24:
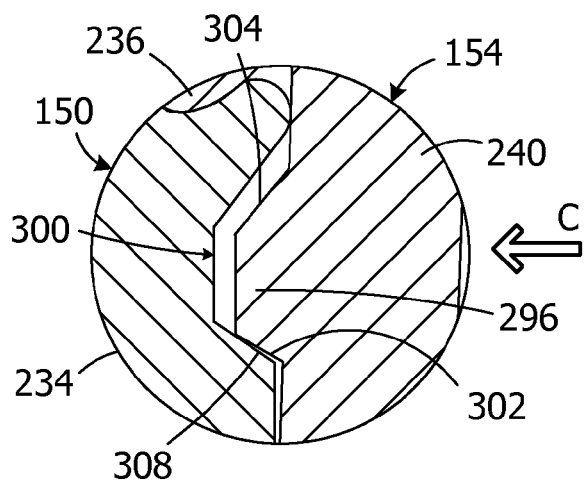
FIG. 24 is a section view of a portion of the sound processor illustrated in FIG. 23.
Figure 25:
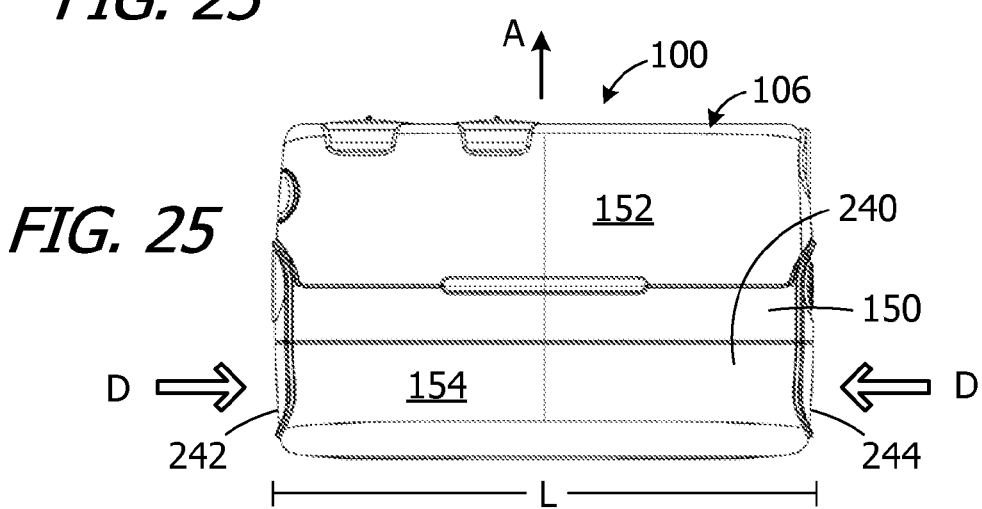
FIG. 25 is a side view of a sound processor in accordance with one embodiment of a present invention.
Figure 26:
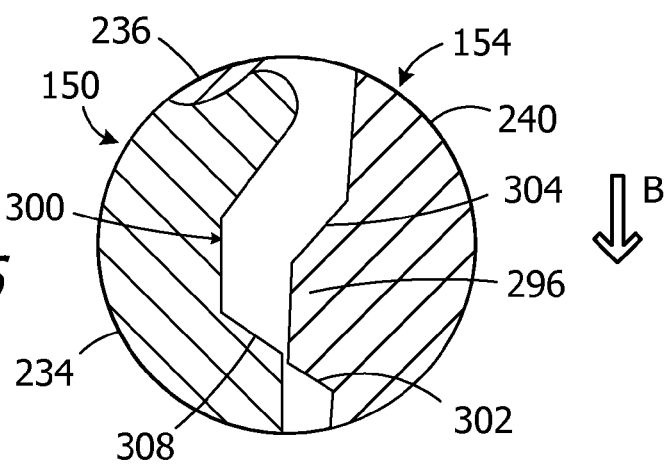
FIG. 26 is a section view of a portion of the sound processor illustrated in FIG. 25 after slight movement from the location illustrated in FIG. 25.

Given the configuration described in the preceding paragraph, its would be extremely difficult, as well as counterintuitive, for a young child to grip the PSR cover at the end walls 232 and 233. The distance between the end walls 232 and 233 is too great to fit within a young child's hand. Instead, when attempting to pull the PSR cover 154 from the main portion housing 150, a young child will grip the PSR cover 154 at the side walls 238 and 240. The distance between side walls 238 and 240 is considerably smaller and, accordingly, they are easier to grip. A gripping force in the direction of arrows C will be applied to the side walls 238 and 240 when applying removal force in the direction of arrows B (FIG. 23). Applying gripping force in the direction of arrows C will, however, prevent the protrusions 294 and 296, which are carried by the PSR cover side walls 238 and 240 (FIG. 21), from moving out of the indentations 298 and 300. The gripping force prevents the PSR cover side walls 238 and 240 from moving radially outwardly. As the young child pulls harder in the direction of arrows B, he/she will also apply more force in the direction of arrows C to maintain a grip on the cover 154, thereby preventing the protrusions 294 and 296 from coming out of the indentations 298 and 300 despite the increase in the pulling force that would otherwise deflect the side walls 238 and 240 radially outwardly.

When an adult who is aware of the present configuration desires to remove the PSR cover 154 from the main portion housing 150, he/she will grip the cover at the end walls 242 and 244 and apply a gripping force in the direction of arrow D (FIG. 25) and removal force in the direction of arrows B (FIG. 23). The cam surfaces 302 on the protrusions 294 and 296 will engage the edges 308 of the side walls 234 and 235 as the cover 154 moves in the direction of arrows B. Because there is no gripping force preventing the cover walls 238 and 240 from deflecting radially outwardly, the protrusions 294 and 296 will move out of the indentations 298 and 300 as the PSR cover 154 in the direction of arrows B, thereby unlocking the cover and permitting removal.

PSR covers may also be provided with structures that facilitate movement of the PSR cover to and from the attached/covered state (FIGS. 16 and 21). More specifically, the robust seal provided by the seal 236 (or 236') may trap air within the power supply receptacle 118 as the PSR cover 154 approaches the attached/covered state during placement of the PSR cover over the power supply receptacle. The pressure of the air (if trapped) will then increase as the PSR cover 154 continues its movement to the attached/covered state, thereby creating a force that opposes the force being applied by the user. Similarly, when the user pulls the PSR cover 154 from the attached/covered state at the outset of the removal process, a suction force that is created by the trapped air will oppose removal of the PSR cover until the PSR cover has moved a distance sufficient to break the seal.

Figure 27:
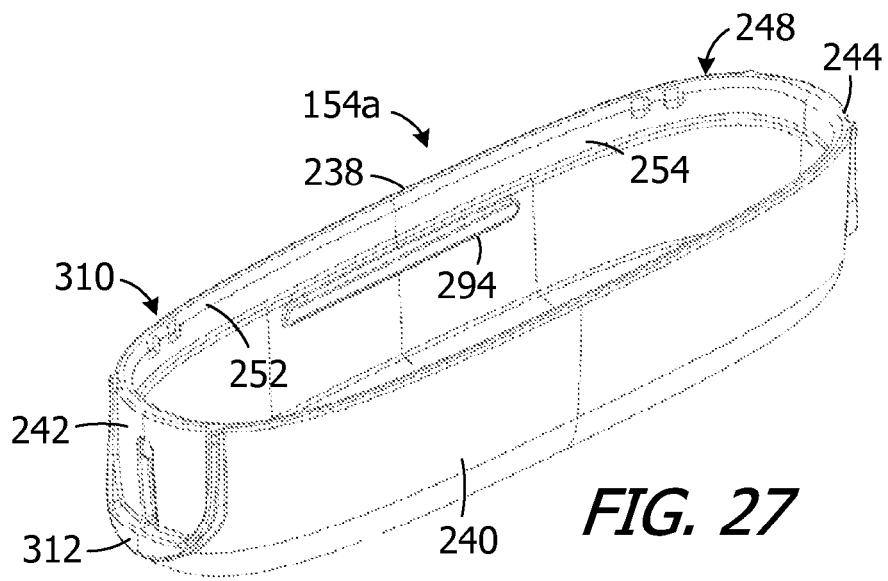
FIG. 27 is a perspective view of a power supply receptacle cover in accordance with one embodiment of a present invention.
Figure 28:
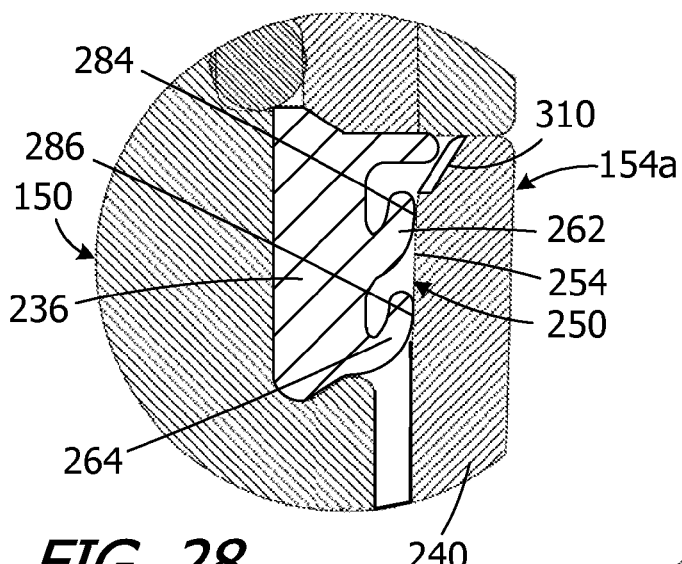
FIG. 28 is a section view of a portion of a sound processor main portion with the power supply receptacle cover illustrated in FIG. 27 in place.

One example of a PSR cover that is configured to vent air without effecting the seal provided by seal 236, and which may be incorporated into any of the sound processors described herein, is generally represented by reference numeral 154a in FIGS. 27 and 28. PSR cover 154a is essentially identical to PSR cover 154 and similar elements are represented by similar reference numerals. The PSR cover 154a also includes one or more vents. The vents may be of any suitable number, form or location. There are four sets of two vents 310 in the illustrated embodiment, with two sets on each side wall 238 and 240. The sets of vents 310 may be located at the same locations on the side walls 238 and 240, as they are in the exemplary embodiment, or may be at different locations.

In the illustrated embodiment, the vents 310 are located in the tapered transition portion 252 and, accordingly, do not effect the seal formed between the cover inner surface seal portion 254 and the seal protrusion 262 (FIG. 28) at contact point 284. However, during placement of the PSR cover 154a onto the housing main portion 150, the vents 310 permit air passage past the seal protrusion 262 and prevent the aforementioned pressure increase within the power supply receptacle 118. Similarly, after the PSR cover 154a has been moved a small distance from the attached/covered state during cover removal, the vents 310 will be aligned with the seal protrusion 262 so that air can be drawn into the power supply receptacle 118, thereby preventing the creation of suction force.

It should also be noted that the vents 310 are located near both longitudinal ends of each of the cover side walls 238 and 240 in the illustrated embodiment. Thus, should the PSR cover 154a be tilted relative to housing main portion 150 when the being placed on the main portion, i.e. should one of the end walls 242 and 244 be closer to the main portion than the other, venting will occur at the trailing vents 310 as the PSR cover straightens out prior to reaching the attached/covered state. Similarly, venting will occur if the user pulls from one end of the PSR cover 154*a* during removal. Venting will occur at all vents 310 during placement and removal when the PSR cover 154*a* is not tilted relative to the housing main portion 150.

The exemplary cover 154*b* illustrated in FIG. 29 is essentially identical to PSR cover 154*a* and similar elements are represented by similar reference numerals. Here, however, the cover 154*b* is configured for use with seal 236'. To that end, the cover includes an inner surface 250*b* without a tapered transition portion. The seal portion 254 extends essentially to the open end 248. The single protrusion 264' forms a seal at contact point 286.

To facilitate movement of the PSR cover 154*b* to and from the attached/covered state, the PSR cover also includes vents 310*b* that may be of any suitable number, form or location. There may be four sets of two vents 310*b*, as is described above with reference to vents 310, with the vents being long enough to extend from about the open end 248 to the illustrated location adjacent to the contact point 286.

The exemplary PSR cover 154*a* illustrated in FIGS. 27 and 28 also includes a protrusion 312 on the cover end walls 242 and 244. The protrusions 312, which help the user grip the end walls 242 and 244, may also be employed on the PSR covers 154 and 154*b*.

Although the inventions disclosed herein have been described in terms of the preferred embodiments above, numerous modifications and/or additions to the above-described preferred embodiments would be readily apparent to one skilled in the art. By way of example, but not limitation, the inventions include any combination of the elements from the various species and embodiments disclosed in the specification that are not already described. Additionally, the inventions described herein are also applicable to BTE sound processors. It is intended that the scope of the present inventions extend to all such modifications and/or additions and that the scope of the present inventions is limited solely by the claims set forth below.

I claim:

1. A method of operating a sound processor having a housing with an exterior, the method comprising the step of:
   transmitting visible light that is representative of an operational aspect of the sound processor through a seal that is compressed by the sound processor housing and that has a portion which extends to the exterior of the sound processor housing.

2. A method as claimed in claim 1, wherein the seal is located between a portion of the housing and a portion of a port.

3. A method as claimed in claim 1, wherein the seal is located between a portion of the housing and a portion of a button.

4. A method as claimed in claim 1, further comprising the step of:
   emitting visible light that is representative of an operational aspect of the sound processor into the seal from a location within the housing.

5. A method as claimed in claim 1, further comprising the steps of:
   emitting visible light of a first color into the seal from a location within the housing in response to a first operational aspect of the sound processor; and
   emitting visible light of a second color into the seal from a location within the housing in response to a second operational aspect of the sound processor.

6. A sound processor, comprising:
   a housing defining an exterior;
   sound processor circuitry within the housing;
   a seal formed at least in part from substantially translucent elastomeric material, the seal being compressed by the sound processor housing and having positioned such that at least a portion of the substantially translucent elastomeric material extends to the housing exterior; and
   a light emitter carried within housing that directs light into the substantially translucent elastomeric material such that the light is visible at the housing exterior.

7. A sound processor as claimed in claim 6, wherein the seal is compressed between a portion of the housing and a portion of a structure associated with the housing exterior.

8. A sound processor as claimed in claim 7, wherein the structure associated with the housing exterior comprises a port.

9. A sound processor as claimed in claim 7, wherein the structure associated with the housing exterior comprises a button.

10. A sound processor as claimed in claim 7, wherein
    the structure associated with the housing exterior includes a cylindrical surface;
    the housing includes a cylindrical surface; and
    the seal includes a cylindrical portion.

11. A sound processor as claimed in claim 6, wherein the seal is formed from at least substantially transparent elastomeric material.

12. A sound processor as claimed in claim 6, wherein
    the housing is formed from relatively hard material; and
    the at least substantially translucent elastomeric material is softer than the relatively hard material.

13. A sound processor as claimed in claim 12, wherein the at least substantially translucent elastomeric material has a hardness of about 40-80 Shore A.

14. A sound processor as claimed in claim 6, wherein the seal includes a compressed protrusion.

15. A sound processor as claimed in claim 6, wherein the light emitter comprises an LED.

16. A sound processor, comprising:
    a housing defining an exterior;
    a device, accessible from the exterior of the housing, carried by the housing such that a gap is defined between a portion of the housing and a portion of the device;
    sound processor circuitry within the housing;
    a light emitter carried within the housing; and
    means, located within the gap, extending to the housing exterior, and associated with the light emitter, for sealing the gap against the ingress of moisture while permitting transmission of light through the gap to the housing exterior.

17. A sound processor as claimed in claim 16, wherein the device comprises a port.

18. A sound processor as claimed in claim 16, wherein the device comprises a button.

19. A sound processor as claimed in claim 16, wherein the light emitter comprises an LED.

* * * * *